United States Patent [19]

Hirasawa et al.

[11] Patent Number: 4,985,198
[45] Date of Patent: Jan. 15, 1991

[54] TOOTH-ADHESIVE COMPOUNDS

[75] Inventors: Tadashi Hirasawa, Tokyo; Ikuro Harashima, Yokohama, both of Japan

[73] Assignee: G-C Dental Industrial Corp., Tokyo, Japan

[21] Appl. No.: 319,889

[22] Filed: Mar. 7, 1989

Related U.S. Application Data

[63] Continuation of Ser. No. 105,282, Oct. 7, 1987, abandoned.

[30] Foreign Application Priority Data

Apr. 28, 1987 [JP] Japan ................................ 62-103220

[51] Int. Cl.$^5$ ............................................. C07C 69/00
[52] U.S. Cl. .................................... 560/130; 560/144; 560/221; 523/116
[58] Field of Search ................. 160/144, 130; 523/116

[56] References Cited

U.S. PATENT DOCUMENTS

| | | | |
|---|---|---|---|
| 4,144,283 | 3/1979 | Matsubara | 560/221 |
| 4,212,989 | 7/1980 | Isshiki et al. | 560/130 |

FOREIGN PATENT DOCUMENTS

| | | | |
|---|---|---|---|
| 0074708 | 3/1983 | European Pat. Off. | |
| 54-11149 | 6/1979 | Japan. | |
| 15468 | 1/1984 | Japan. | |
| 9070643 | 4/1984 | Japan | 560/221 |
| 129278 | 7/1984 | Japan. | |

OTHER PUBLICATIONS

J. Biomed. Mater. Res., vol. 9, pp. 501–510 (1975); R. L. Bowen: Adhesive Bonding of Various Materials to Hard Tooth Tissues, IX. The Concept of Polyfunctional Surface-Active Comonomers.

Journal of Japanese Society for Dental Apparatus and Materials, vol. 8, No. 14, (1967), Studies on Adhesive Filling Materials to Hard Tooth Tissues, Part 1.

*Primary Examiner*—Paul J. Killos
*Attorney, Agent, or Firm*—Oblon, Spivak, McClelland, Maier & Neustadt

[57] ABSTRACT

A tooth-adhesive compound is expressed in terms of the following general formula:

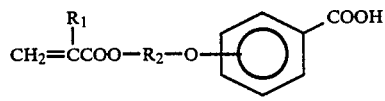

wherein
$R_1$ is a hydrogen atom or a methyl group, and
$R_2$ may or may not be present; and if present, $R_2$ is an alkylene group having 1 to 4 carbon atoms or a $-CH_2-CH_2)_nO-CH_2-CH_2-$ group in which $n=1$ or 2, and a substituent containing $R_1$ and $R_2$ is located at the o-, m- or p-position with respect to the carboxyl group bonded to the phenyl group.

4 Claims, No Drawings

TOOTH-ADHESIVE COMPOUNDS

This application is a continuation of application Ser. No. 07/105,282, filed on Oct. 7, 1987, now abandoned.

BACKGROUND OF THE INVENTION

1. Field of the Invention

This invention relates to a tooth-adhesive compound to be applied as dental adhesives and filling materials, which may be used alone or in the form of copolymers with other vinyl compounds.

2. Statement of the Prior Art

Hitherto, methyl methacrylate polymers or their compolymers with other vinyl compounds have been used as the dental adhesives. However, none of such polymers and copolymers have had any satisfactory adhesion to tooth substrates, especially to dentin.

For prosthetic or filling restoration, therefore, restorative materials had to be fixed and retained by mechanical means depending upon the restoration form. This has offered a problem that healthy tooth must be excessively ground.

SUMMARY OF THE INVENTION

It is a main object of the present invention to enable a tooth-adhesive compound, e.g., 3-methyacryloyloxybenzoic acid, alone or a resin containing it to be used as adhesives or filling materials, whereby the adhesive strength and adhesion stability to tooth are increased and enhanced.

According to the present invention, that object is achieved by a compound expressed in terms of the following general formula:

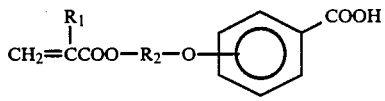

wherein $R_1$ is a hydrogen atom or a methyl group, and $R_2$ may or may not be present; and if present, $R_2$ represents an alkylene group having 1 to 4 carbon atoms or a $-(CH_2-CH_2-O)_n CH_2-CH_2-$group in which $n=1$ or 2, and a substituent containing $R_1$ and $R_2$ is located at the o-, m- or p-position with respect to the carboxyl group bonded to the phenyl group. The compound according to the present invention is of polymerizability and, at the same time, shows high affinity to tooth, and forms a high-strength and stable adhesion to tooth in a wet environment in the mouth cavity.

DETAILED DESCRIPTION OF THE INVENTION

According to the present invention, there is provided a compound expressed in terms of the following general formula:

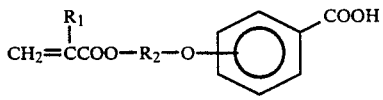

wherein $R_1$ is a hydrogen atom or a methyl group, and $R_2$ may not be present. If present, $R_2$ is then an alkylene group having 1 to 4 carbon atoms or a $-(CH_2-CH_2-O)_n CH_2-CH_2$-group in which $n=1$ or 2, and a substituent containing $R_1$ and $R_2$ is located at the o-, m- or p-position with respect to the carboxyl group bonded to the phenyl group.

By way of example, the preparation of the compounds according to the present invention will now be explained with reference to 2-methacryloyloxybenzoic acid.

In a four-necked flask of 500 ml equipped with a stirrer, a thermometer, a condenser having a calcium chloride tube and a dropping funnel having a branched pipe of 50 ml, 27.6 grams (0.2 moles) of salicylic acid and 20.9 grams (0.2 moles) of methacryloyl chloride are dissolved in 200 ml of dry ether. Apart from this, 50 ml of a solution of 15.8 grams (0.2 moles) of dry pyridine in dry ether are put into the dropping funnel. While the interior of the flask is cooled and maintained at about 5° C., the content of the dropping funnel is added dropwise to the flask. After the completion of dropwise addition, stirring is continued at about 5° C., for 2 hours and then at room temperature overnight to bring the reaction to an end. The precipitated pyridine hydrochloride is filtrated out, and a slight amount of p-methoxyphenol is added to the ether filtrate as the polymerization inhibiter, followed by distillation-off of the ether under reduced pressure. The solid residues are recrystallized three times from n-hexane for purification, yielding 5.0 grams of pure crystals having a melting point of 92° C. to 95° C.

The infrared absorption spectra of the purified crystals were found to include a wide band of 3200–2500 cm$^{-1}$ and a band of 1690 cm$^{-1}$ showing the presence of a carboxyl group, bands of 1740 cm$^{-1}$, 1270 cm$^{-1}$ and 1120 cm$^{-1}$ showing the presence of an ester, a band of 1640 cm$^{-1}$ showing the presence of a double bond and a band of 1600 cm$^{-1}$ showing the presence of a phenyl group. From the proton nuclear magnetic resonance spectra, an absorption band of δ 2.08 showing the presence of a methyl group was found at the integration intensity of 3 and bands of δ 5.76 and δ 6.37 showing the presence of H$_2$C= were also found at the respective integration intensity of 1. Further, absorption bands of δ 7.18, δ 7.36, δ 7.63 and δ 8.12 showing the presence of an o-substituted benzene at an integration intensity of 1 were obtained in the form of quartet, sextet, octet and quartet. The results of elementary analysis were carbon: hydrogen=63.84:4.89 (Calculated; carbon:hydrogen=64.07:4.89). From the foregoing results, the obtained synthetic compound was identified as 2-methacryloyloxybenzoic acid.

EXAMPLES

The adhesion of 2-, 3- or 4-methacryloyloxybenzoic acid to tooth was measured.

EXAMPLES 1

Application Sample: Bovine enamel
Adhesive Composition:
  (a) 2-methacryloyloxybenzoic acid+methyl methacrylate+polymethyl methacrylate
  (b) 3-methacryloyloxybenzoic acid+methyl methacrylate+polymethyl methacrylate
  (c) 4-methacryloyloxybenzoic acid+methyl methacrylate+polymethyl methacrylate Enamel was obtained by polishing the labial surface of a bovine tooth by means of No. 1000 emery paper under a water stream, and was applied thereover with a cellophane tape (about 10×10 mm) provided with a round hole having a diameter of 3 mm. As the polymerization initiator, partially oxidized tri-n-butyl borane was used. An adhesive composition obtained by adding a small amount of polymethyl methacrylate powders to a mixture of 5% by weight of 2-methacryloyloxybenzoic acid and 95% by weight of methyl methacrylate was applied over the aforesaid round hole by means of a small brush to bond an acryl rod to the bovine tooth enamel. In a similar manner, acryl rods were bonded to the bovine tooth enamel with adhesive compositions in which 5% by weight of 3-methacryloyloxybenzoic acid and 1% by weight of 4-methacryloyloxybenzoic acid were used in lieu of 2-methacryloyloxybenzoic acid. After the lapse of 30 minutes, the acryl rods with the bovine teeth bonded thereto were immersed in water of 37° C. for 24 hours. After the bovine teeth had been taken out of the water, the bond strengths thereof to the acryl rods were measured at a rate of tension 1 mm/min. with a Shimazu Autograph IS-500 Type. The same shall hereinafter apply to the measurement of the bond strength.

Comparative Example 1

Example 1 was repeated, except that use was made of methyl methacrylate containing no methacryloyloxybenzoic acids.

EXAMPLE 2

Application Sample: Bovine dentin
Adhesive Composition: The same as used in Ex. 1

Example 1 was repeated, except that in place of the enamel, use was made of the dentin obtained by carefully grinding off the enamel of the labial surface of an anterior teeth of cattle under a water stream, said dentin being smoothly polished in the same way in Ex. 1.

Comparative Example 2

Example 2 was repeated, except that methyl methacrylate containing no methacryloyloxybenzoic acid was substituted for the adhesive composition used in Ex. 2.

The results of Examples 1 and 2 as well as those of Comparison Examples 1 and 2 are set forth in Table 1.

TABLE 1

| Adhesive Composition (weight %) | | Bond Strength (kgf/cm²) | |
|---|---|---|---|
| | | Enamel | Dentin |
| Examples 1, 2 | 2-methacryloyloxybenzoic acid | 5 | 35 | 37 |
| | Methyl methacrylate | 95 | | |
| | 3-methacryloyloxybenzoic acid | 5 | 42 | 45 |
| | Methyl methacrylate | 95 | | |
| | 4-methacryloyloxybenzoic acid | 1 | 39 | 40 |
| | Methyl methacrylate | 99 | | |
| Comparison Examples 1, 2 | Methyl methacrylate | 100 | 16 | 25 |

EXAMPLE 3

Application Sample: Bovine enamel and bovine dentin treated with an aqueous solution containing citric acid and iron (III) chloride.
Adhesive Composition: The same as used in Ex. 1.

The bovine enamel described in Ex. 1 and the bovine dentin described in Ex. 2 were respectively treated with an aqueous solution containing 10% by weight of citric acid and 3% by weight of iron (III) chloride for 30 seconds. In the same manner as described in Ex. 1, acryl rods were bonded to the bovine teeth for the measurement of the bond strength therebetween.

Comparison Example 3

Example 3 was repeated, except that methyl methacrylate containing no methacryloyloxybenzoic acid was used in place of the adhesive composition employed in Ex. 3.

The results of Ex. 3. and those of Comparison Example 3 are set forth in Table 2.

TABLE 2

| Adhesive Composition (weight %) | | | Bond Strength (kgf/cm²) | |
|---|---|---|---|---|
| | | | Enamel | Dentin |
| Example 3 | 2-methacryloyloxybenzoic acid | 5 | 121 | 134 |
| | Methyl methacrylate | 95 | | |
| | 3-methacryloyloxybenzoic acid | 5 | 148 | 156 |
| | Methyl methacrylate | 95 | | |
| | 4-methacryloyloxybenzoic acid | 1 | 123 | 147 |
| | Methyl methacrylate | 99 | | |
| Comparison Example 3 | Methyl methacrylate | 100 | 111 | 105 |

EXAMPLE 4

Application Sample: Bovine dentin treated with an aqueous solution containing citric acid and iron (III) Chloride.
Adhesive Composition: The same as used in Ex. 3.

Example 3 was repeated. However, the treated bovine dentins with acryl rods bonded thereto were immersed in water of 37° C. for one, four, eight and twelve weeks, until the bond strengths therebetween were measured.

Comparison Example 4

Ex. 4 was repeated. However, any methacryloyloxybenzoic acid was not used, and methyl methacrylate was used as the monomer.

The results of Ex. 4 and those of Comparison Example 4 are set forth in Table 3.

TABLE 3

| Adhesive Composition (weight %) | | | Bond Strength (kgf/cm²) | | | |
|---|---|---|---|---|---|---|
| | | | 1 week after immersion in water | 4 weeks after immersion in water | 8 weeks after immersion in water | 12 weeks after immersion in water |
| Example 4 | 2-methacryloyloxy-benzoic acid | 5 | 135 | 126 | 115 | 84 |
| | Methyl methacrylate | 95 | | | | |
| | 3-methacryloyloxy- | 5 | 138 | 138 | 124 | 96 |

TABLE 3-continued

| Adhesive Composition (weight %) | | | Bond Strength (kgf/cm²) | | | |
|---|---|---|---|---|---|---|
| | | | 1 week after immersion in water | 4 weeks after immersion in water | 8 weeks after immersion in water | 12 weeks after immersion in water |
| | benzoic acid | | | | | |
| | Methyl methacrylate | 95 | | | | |
| | 4-methacryloyloxy-benzoic acid | 1 | 136 | 97 | 83 | 47 |
| | Methyl methacrylate | 99 | | | | |
| Comparison Example 4 | Methyl methacrylate | 100 | 93 | 76 | 84 | 44 |

EXAMPLE 5

Application Sample: The same as used in Ex. 3.
Adhesive Composition: The same as used in Ex. 3.

In the same manner as described in Ex. 3, an acryl rod was bonded to tooth, and was immersed in water of 37° C. for 24 hours. The test piece was then immersed 60 times alternately in water of 4° C. and water of 60° C. every minute for a total time of 2 hours. Afterwards, the bond strength between the sample and the adhesive composition was measured.

Comparison Example 5

An experiment similar to that of Ex. 4 was conducted for the measurement of the bond strength. However, any methacryloyloxybenzoic acid was not used, and only methyl methacrylate was employed as the monomer.

The results of Ex. 5 and Comparison Example 5 are set forth in Table 4.

TABLE 4

| Adhesive Composition (weight %) | | | Bond Strength (kgf/cm²) | |
|---|---|---|---|---|
| | | | Enamel | Dentin |
| Example 5 | 2-methacryloyloxybenzoic acid | 5 | 142 | 117 |
| | Methyl methacrylate | 95 | | |
| | 3-methacryloyloxybenzoic acid | 5 | 140 | 147 |
| | Methyl methacrylate | 95 | | |
| | 4-methacryloyloxybenzoic acid | 1 | 149 | 142 |
| | Methyl methacrylate | 99 | | |
| Comparison Example 5 | Methyl methacrylate | 100 | 104 | 63 |

EXAMPLE 6

Application Sample: The same as used in Ex. 3.
Adhesive Composition: 3-methacryloyloxybenzoic acid + methyl methacrylate + polymethyl methacrylate.

Example 3 was repeated. As the adhesive composition, however, use was made of a combination of a powdery mixture obtained by adding 2 parts by weight of a polymerization initiator benzoyl peroxide to 100 parts by weight of polymethyl methacrylate with a liquid mixture obtained by adding 1 parts by weight of a polymerization accelerator, N,N-di(2-hydroxyethyl)-p-toluidine to 100 parts by weight of the 3-methacryloyloxybenzoic acid composition used in Ex. 1.

Comparison Example 6

Example 6 was repeated, provided however that 3-methacryloyloxybenzoic acid was not used.

The results of Ex. 6 and Comparison Example 6 are tabulated in Table 5.

TABLE 5

| Adhesive Composition (weight %) | | | Bond Strength (kgf/cm²) | |
|---|---|---|---|---|
| | | | Enamel | Dentin |
| Example 6 | 3-methacryloyloxybenzoic acid | 5 | 65 | 26 |
| | Methyl methacrylate | 95 | | |
| Comparison Example 6 | Methyl methacrylate | 100 | 32 | 1 |

EXAMPLE 7

Application Sample: The same as used in Ex. 3.
Adhesive Composition: 3-methacryloyloxybenzoic acid + methyl methacrylate Example 6 was repeated, provided however that 2 parts by weight of sodium p-toluenesulfinate was added to the powdery mixture used in Ex. 6.

Comparison Example 7

Example 7 was repeated, provided however, that 3-methyacryloyloxybenzoic acid was not used.

The results of Example 7 and those of Comparison Example 7 are tabulated in Table 6.

TABLE 6

| Adhesive Composition (weight %) | | | Bond Strength (kgf/cm²) | |
|---|---|---|---|---|
| | | | Enamel | Dentin |
| Example 7 | 3-methacryloyloxybenzoic acid | 5 | 99 | 47 |
| | Methyl methacrylate | 95 | | |
| Comparison Example 7 | Methyl methacrylate | 100 | 48 | 6 |

The compounds defined in the present invention show good copolymerizability with respect to the known methacrylates or acrylates generally used with dental resinous materials, and allow such resinous materials to be added to tooth with large strength, while permitting the adhesion therebetween to be stably maintained.

As will be clearly appreciated from the results of Examples 1 to 7, adhesive strength and adhesion stability are enhanced and improved by the addition of a small amount of the present compounds to methyl methacrylate. As will also be noted from the results of Examples 6 and 7 in particular, the compounds according to the present invention are characterized in that the adhesion of dental resinous materials to tooth is increased to a practically usable adhesive strength without recourse to a polymerization initiator such as partially oxidized tri-n-butyl borane which presents a little problem in connection with storability.

What is claimed is:

1. A dental adhesive comprising a compound of the formula:

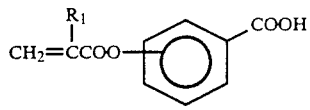

wherein $R_1$ is a hydrogen atom or a methyl group, and the substituent containing $R_1$ is located at the o-, m- or p-position with respect to the carboxyl group bonded to the phenyl group.

2. The dental adhesive of claim 1, wherein the compound is 2-methacryloyloxybenzoic acid.

3. The dental adhesive of claim 1, wherein the compound is 3-methacryloyloxybenzoic acid.

4. The dental adhesive of claim 1, wherein the compound is 4-methacryloyloxybenzoic acid.

* * * * *